(12) United States Patent
Kim

(10) Patent No.: US 11,357,954 B2
(45) Date of Patent: Jun. 14, 2022

(54) MEDICAL APPARATUS

(71) Applicant: JUVENUI Co., Ltd., Gyeonggi-do (KR)

(72) Inventor: Hyun Hong Kim, Gyeonggi-do (KR)

(73) Assignee: JUVENUI CO., LTD.

( * ) Notice: Subject to any disclaimer, the term of this patent is extended or adjusted under 35 U.S.C. 154(b) by 308 days.

(21) Appl. No.: 16/168,998

(22) Filed: Oct. 24, 2018

(65) Prior Publication Data

US 2019/0125399 A1   May 2, 2019

(30) Foreign Application Priority Data

Oct. 26, 2017 (KR) ........................ 10-2017-0140154

(51) Int. Cl.
  *A61M 25/01*     (2006.01)
  *A61M 25/10*     (2013.01)
  (Continued)

(52) U.S. Cl.
  CPC .... *A61M 25/0147* (2013.01); *A61M 25/0105* (2013.01); *A61M 25/0133* (2013.01);
  (Continued)

(58) Field of Classification Search
  CPC .......... A61M 25/0023; A61M 25/0026; A61M 25/0032; A61M 25/0074; A61M 25/0147; A61M 2025/0024; A61M 2025/0037; A61M 2025/0079; A61M 2025/015; A61M 2025/0063; A61M 2025/0186; A61M 2025/1093; A61M 25/0071; A61M 25/0102; A61M 25/0105; A61M 25/0133; A61M 25/0144; A61M 25/09; A61M 25/10; A61B 2017/00323; A61B 17/22; A61B 17/3401; A61B 17/3415; A61B 2017/3445

See application file for complete search history.

(56) References Cited

U.S. PATENT DOCUMENTS 5,273,535 A * 12/1993 Edwards ........... A61M 25/0136
  600/585
6,007,531 A * 12/1999 Snoke .................. A61B 1/0052
  604/95.04

(Continued)

FOREIGN PATENT DOCUMENTS

KR  1 0-2014-0047342 A    4/2014
WO  WO-2015115504 A1 *  8/2015  ........ A61M 25/0133

*Primary Examiner* — Shefali D Patel
(74) *Attorney, Agent, or Firm* — Renaissance IP Law Group LLP

(57) ABSTRACT

A medical apparatus according to one embodiment of the present invention can be used for dissociating adhesion to an epidural space and alleviating stenosis to a spinal canal; and comprises: an insertion part including a first end configured to be inserted into a human body and a second end opposite to the first end, and having a first through hole extended from the first end to the second end and formed inside the insertion part, an expansion part configured to be expandable and formed on an outer surface of the insertion part at a predetermined distance apart from the first end of the insertion part, a pair of wires extending in the insertion part and fixed to a region of the first end of the insertion part, a main body, a dial installed to the main body, and a rotation control part coupled to the dial.

12 Claims, 17 Drawing Sheets

(51) Int. Cl.
*A61B 17/34* (2006.01)
*A61M 25/09* (2006.01)
*A61B 17/22* (2006.01)
*A61K 9/00* (2006.01)
*A61M 25/00* (2006.01)
*A61B 17/32* (2006.01)
*A61B 17/00* (2006.01)

(52) U.S. Cl.
CPC .............. *A61M 25/10* (2013.01); *A61B 17/22* (2013.01); *A61B 17/320016* (2013.01); *A61B 17/3401* (2013.01); *A61B 17/3415* (2013.01); *A61B 2017/00323* (2013.01); *A61B 2017/22038* (2013.01); *A61B 2017/320048* (2013.01); *A61B 2017/3445* (2013.01); *A61B 2217/007* (2013.01); *A61K 9/0019* (2013.01); *A61M 25/0102* (2013.01); *A61M 25/09* (2013.01); *A61M 2025/0007* (2013.01); *A61M 2025/0063* (2013.01); *A61M 2025/015* (2013.01); *A61M 2025/1093* (2013.01)

(56) References Cited

U.S. PATENT DOCUMENTS

| | | | |
|---|---|---|---|
| 8,430,864 B2* | 4/2013 | Schultz | A61M 25/0136 604/528 |
| 8,808,169 B2* | 8/2014 | Macnamara | A61B 1/0057 600/149 |
| 2003/0004460 A1* | 1/2003 | Bedell | A61M 25/0136 604/95.04 |
| 2012/0101511 A1* | 4/2012 | You | A61B 17/32 606/159 |
| 2014/0155815 A1* | 6/2014 | Fulton, III | A61M 25/04 604/27 |

\* cited by examiner

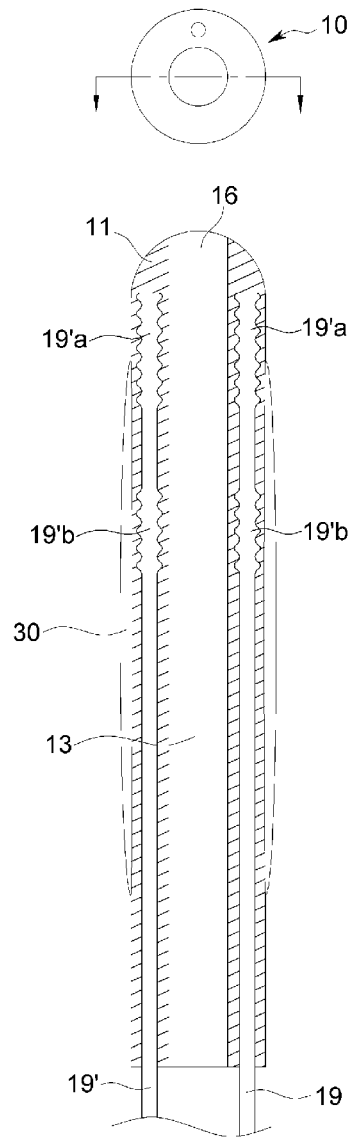

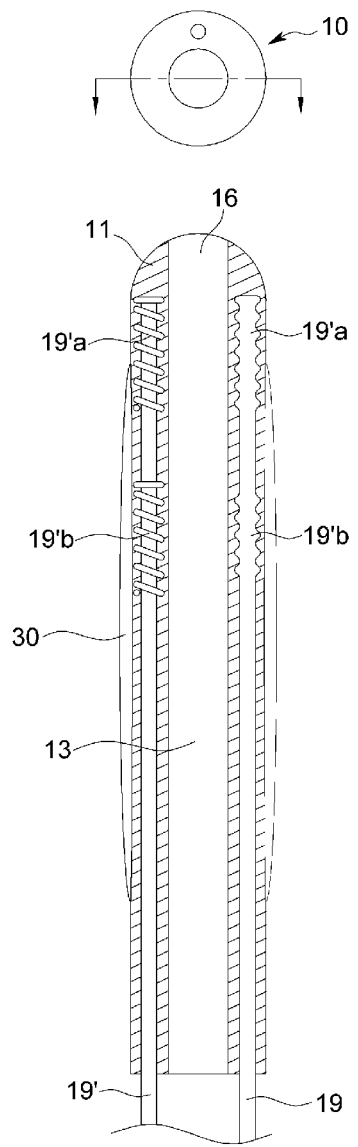

MEDICAL APPARATUS

CROSS REFERENCE TO RELATED APPLICATIONS

This application claims the benefit of and priority to Korean Patent Application No. 10-2017-0140154, filed on 26 Oct. 2017. The entire disclosure of the applications identified in this paragraph are incorporated herein by references.

FIELD

The present invention relates to a medical apparatus for dissociating adhesion to an epidural space and alleviating stenosis to a spinal canal.

BACKGROUND

A low back pain is collectively referring to the pain of the back and legs, and is one of the diseases that anyone can suffer during their lives. The low back pain is the second most common symptom of a cold in adults of 55 or less years of age that cause a job absenteeism, and is followed by a headache among the causes of a chronic pain.

Recently, there have been an increase in the number of patients returning to the hospital due to a so-called failed back surgery syndrome, which causes the recurrence or aggravation of the low back pain after surgery with the surge of a spinal surgery, and this has been known to be the main cause of the pain caused by adhesion and fibrosis in the epidural space, the outer part of the dura surrounding a spinal cord. The epidural space is the space between the dura and the spinal canal, which is the protective membrane surrounding the spinal cord, and is a tissue rich in a nerve fiber, an adipose tissue, a connective tissue, a blood vessel and a lymphatic vessel. The epidural space can be divided into an anterior epidural space and a posterior epidural space. The anterior epidural space is surrounded by a yellow ligament and a periosteum of a vertebral body. A centrum, an intervertebral disc and a posterior longitudinal ligament are located on the front side of the anterior epidural space, and a dura is positioned on the back side thereof. The anteroposterior diameter of the anterior epidural space is 1.3 to 2.2 mm in a lumbar region, and the anteroposterior diameter of the posterior epidural space is known to be 2.0 to 6.0 mm.

Adhesion to the epidural space occurs after spinal surgery in many cases, but it also occurs frequently in a disc herniation, a degenerative spinal stenosis, and the likes.

While in the disc herniation, the adhesion occurs as a nucleus pulposus in the disc leaks laterally or backward through the tear gap of a posterior annulus fibrosus to cause deposition of cells in the epidural space and inflammatory reaction, the adhesion in the spinal stenosis occurs by inflammatory mediators. However, a patient with a chronic low back pain is considered to accompany significant adhesion regardless of a certain cause. The adhesion to the epidural space can cause pain by interfering with inflammation of a nerve root in the epidural space and movement of a dural sleeve of the nerve root. This adhesion also interferes with the flow of venous blood in the epidural space and cause an edema of the nerve root. Therefore, if there is adhesion between the dura and the posterior longitudinal ligament, this adhesion itself may be the cause of pain, and the chemical stimulation of the dura and the nerve root may cause pain. In other words, an abnormal amount of inflammatory substance such as substance P, calcium gene-related peptide, c-fos, phospholipase A2 is present in the anterior epidural space of the stressed nerve tissue, which results in occurrence of the inflammatory reaction and cause of the pain.

Another major cause of the low back pain is a spinal stenosis which results from narrowing of the spinal canal or the intervertebral foramen through which a nerve passes, by an intervertebral joint, a yellow ligament, a disc, and the likes, constituting the spinal canal.

When these two diseases cause the low back pain, a patient feels severe pain in his/her lumbar region and lower extremities, and in some cases he/her cannot walk long away.

A best method for treating these two diseases is to remove adhesion in the case of the adhesion to the epidural space, and to widen the stenosis part to alleviate pressure in a nerve and a blood vessel in case of the stenosis to the spinal canal. Of course, if the above treatment is performed through surgery, it is advantageous to remove the root cause of pain. However, since it costs a lot of money, and the frequency of operation failure and recurrence is increasing, a non-surgical method has been mainly tried recently.

Typically, there is a treatment method of inserting a needle into the intervertebral foramen of the epidural space or the spinal site concerned and injecting a drug that suppresses inflammation or edema. However, in case of the adhesion, the drug does not reach or spread sufficiently at the target site, and in case the adhesion is severe and the fibrosis progresses, it hardly responds to the anti-inflammatory action of steroids, thereby limiting the relief of symptom and making the outcome of the treatment poor. Therefore, there has been a need for a medical apparatus for more effectively and safely alleviating the adhesion to the epidural space and the stenosis to the spinal canal.

Patent Literature: Korean Patent Laid-Open Publication No. 2014-0047342

SUMMARY

The present invention relates to a medical apparatus which can be used for patients with a low back pain according to the adhesion to an epidural apace and the stenosis to a spinal canal, and is aimed to a medical apparatus that can dissociate the adhesion to the epidural space and alleviate to the stenosis to the spinal canal.

Further, the present disclosure provides a medical apparatus comprising an expansion part which can carry out safer and more aggressive surgical procedure with less risk of damage to the human body.

Furthermore, the present disclosure provides a medical apparatus that can more safely and easily adjust the rotation angle of a movable end so as to prevent damage to the internal tissue of the human body by the movable end during the procedure.

A medical apparatus according to one embodiment of the present invention can be used for dissociating adhesion to an epidural space and alleviating stenosis to a spinal canal; and comprises: an insertion part including a first end configured to be inserted into a human body and a second end opposite to the first end, and having a first through hole extended from the first end to the second end and formed inside the insertion part, an expansion part configured to be expandable and formed on an outer surface of the insertion part at a predetermined distance apart from the first end of the insertion part, a pair of wires extending in the insertion part and fixed to a region of the first end of the insertion part, the pair of wires being capable of causing bending of the insertion part by pulling out at least one of the wires, a main body connected to the insertion part at the second end thereof, a dial installed to the main body rotatably and connected to the pair of the wires, and a rotation control part coupled to the dial, and configured to limit rotation of the dial so that the rotation is no longer performed when the dial is rotated over a predetermined angle.

According to one aspect of the present invention, the rotation control part may include at least one of a first rotation control unit that allows the dial to rotate at a first angle or less and a second rotation control unit that allows the dial to rotate at a second angle or less different from the first angle. This makes it possible to change the limit of the rotation angle of the dial in a situation where the load that can withstand the thickness or the material of the ends of the insertion part is different from each other.

According to one aspect of the present invention, the rotation control part includes both of a first rotation control unit and a second rotation control unit, and the first rotation control unit and the second rotation control unit may be formed integrally.

According to one aspect of the present invention, the first rotation control unit or the second rotation control unit can contact a stopper formed on the main body to limit rotation of the dial. Further, the position of such rotation control part can be set such that one of the first rotation control unit and the second rotation control unit is placed at a position that is in contact with the stopper.

The position of the first rotation control unit or the second rotation control unit can be set between a position directed toward the outside of the rotation control part and that directed toward the inside of the rotation control part.

According to one aspect of the present invention, the expansion part may be an expansion structure made of a mesh structure.

According to one aspect of the present invention, the expansion structure may be made of a radiation-impermeable material.

According to one aspect of the present invention, an expansion structure wire for expanding or contracting the expansion structure is provided inside the insertion part, and one end portion of the expansion structure wire can be connected to the expansion structure.

According to one aspect of the present invention, the expansion structure includes a first end region directing toward the first end of the insertion part and a second end region directing toward the second end of the insertion part, wherein the first end region is not fixed to the insertion part, the second end region is fixed to the insertion part, and the expansion structure wire can be connected to the unfixed first end region.

According to one aspect of the present invention, a medical apparatus may include a first injection port formed between a second end of the insertion part and a dial and communicating with a first through hole to inject a drug or insert a medical instrument, and a pair of second injection ports formed on both sides of first injection port, respectively, to inject a drug different from the drug injected into the first injection port or an irrigation fluid so as to clean the medical instrument or bleeding in the body tissue.

According to one aspect of the invention, the medical instrument may comprise a catheter and an endoscope.

According to one aspect of the present invention, a pair of the second injection ports communicate with a T-shaped passage formed in inside the main body, and the T-shaped passage can communicate with a second through hole formed inside the insertion part.

According to one aspect of the present invention, at least one of the pair of the wires may have a spring shape or a concave-convex shape at a portion fixed to the region of the first end of the insertion part.

According to one aspect of the invention, the insertion part comprises a flexible portion made of a flexible material between the expansion part and the second end of the insertion part.

According to one embodiment of the present invention, the therapeutic effect of a low back pain can be maximized by physically alleviating the adhesion to an epidural space and the stenosis to a spinal canal, with an expansion part, a movable end and the likes.

Further, according to an embodiment of the present invention, by more precisely and simply adjusting and restricting the rotation angle of a dial through a rotation control part including at least two portions having different thicknesses, damage to the tissues in the body caused due to an insertion part or a movable end of the insertion part during rotation of the dial to left/right can be prevented.

In addition, according to an embodiment of the present invention, by implementing an expansion part as an expansion structure made of a mesh structure, it is possible to obtain the effect of physically relieving the adhesion and the stenosis like the expansion part operated with a fluid injection, to exclude the risk of damage to the body due to a sharp object, to positively perform a surgical procedure by a high mechanical strength, and to exactly control an expansion amount of the expansion part with a simple operation to secure a more stable and predictable procedure.

BRIEF DESCRIPTION OF THE DRAWINGS

FIG. 3a, FIG. 3a1, FIG. 3a2, and FIG. 3b are enlarged views of an end portion of an insertion part in a medical apparatus according to the embodiment of the present invention.

DETAILED DESCRIPTION

Hereinafter, embodiments of the present invention will be described with reference to the accompanying drawings.

FIG. 1 to FIG. 10 show the elements constituting a medical apparatus 1 and a medical apparatus 100 according to an embodiment of the present invention.

Figure 1:
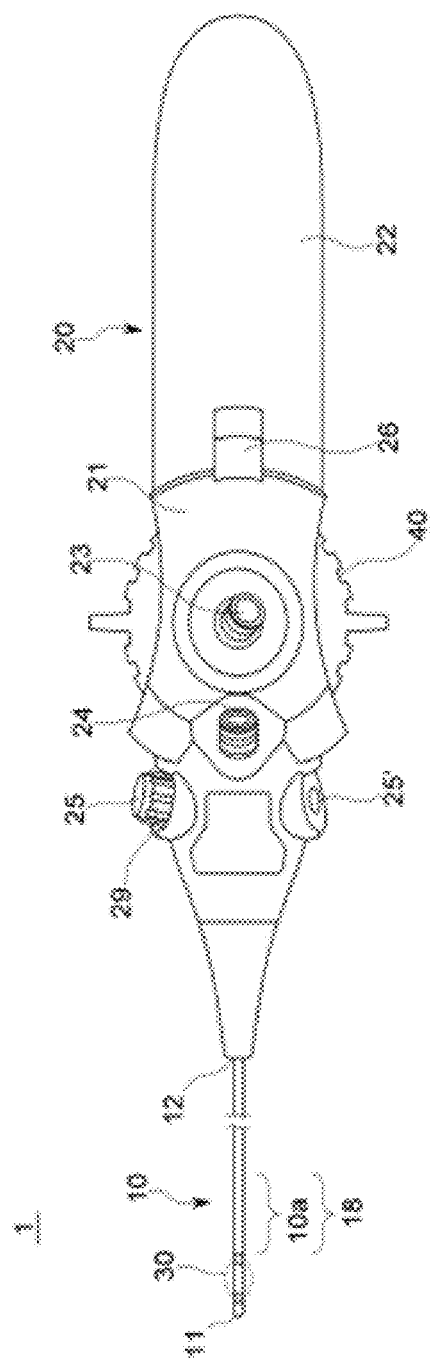
FIG. 1 is a top view of a medical apparatus according to an embodiment of the present invention.
Figure 2:
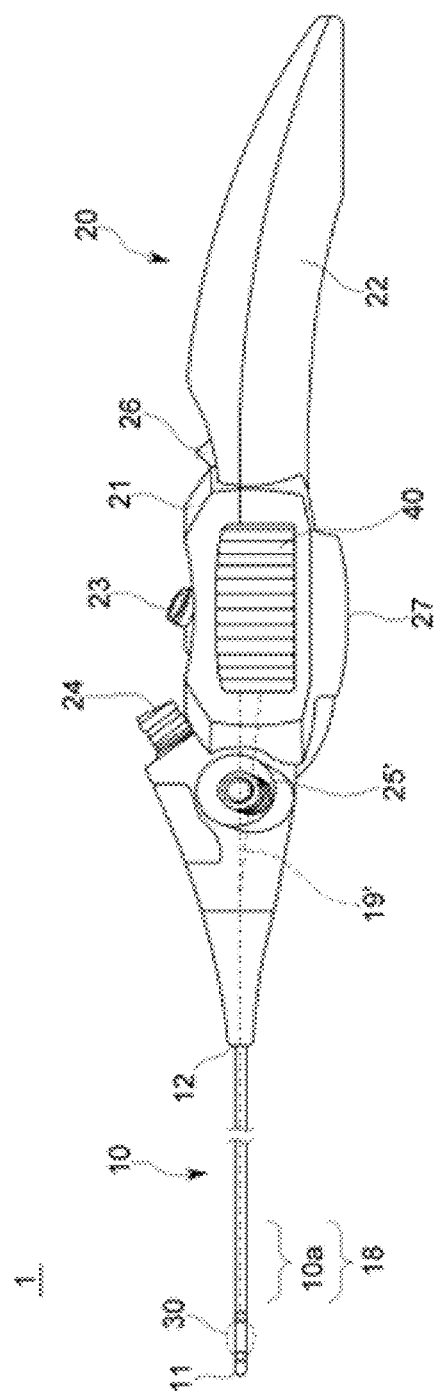
FIG. 2 is a side view of a medical apparatus according to an embodiment of the present invention.

Specifically, FIG. 1 is a top view of a medical apparatus 1 according to an embodiment of the present invention, and FIG. 2 is a side view of a medical apparatus 1 according to an embodiment of the present invention.

As shown in FIGS. 1 and 2 of the present application, the medical apparatus 1 of the present invention may consist of an insertion part 10 and a main body 20.

The insertion part 10 includes a first end 11 configured to be inserted into a human body and a second end 12 opposite to the first end 11. The main body 20 is connected to the second end 12 of the insertion part 10. The main body 20 includes a dial operating portion 21 for operating a dial 40 and a handle portion 22.

FIGS. 3a, 3a1, 3a2, and 3b are enlarged views of an end portion of the insertion part 10 in the medical apparatus 1 according to an embodiment of the present invention. As shown in FIGS. 3a, 3a1, 3a2, and 3b, a first through hole 13 extending from the first end 11 to the second end 12 of the insertion part 10 is formed inside the insertion part 10. The first end 11 of the insertion part 10 is provided with a first hole 16 to which can inject a drug or insert a medical instrument into a human body in communication with the first through hole 13. Through the first hole 16, a drug can be injected or a medical instrument can be accessed into a desired region of the human body. The medical instrument includes, for example, a catheter for injecting a drug or an endoscope, and the first through hole 13 and the first hole 16 of the insertion part 10 can function as a passage for injecting the drug directly or as a guide passage for inserting the catheter for injecting the drug or the endoscope.

The inside of the insertion part 10 is provided with a pair of wires 19 and 19' for operating the insertion part 10. One end of a pair of the wires 19 and 19' may be fixed to the area of the first end 11 of the insertion part 10 and the other end of a pair of the wires 19 and 19' may be extended toward the second end 12 of the insertion part 10. A pair of the wires 19, 19' may be extended so as not to be exposed to the outside through the inside of the insertion part 10.

The other end of a pair of the wires 19, 19' is connected to a dial 40 which is rotatably installed in the main body 20. For example, a connection pipe through which a pair of the wires 19 and 19' can pass is formed in the inside of the main body 20, and a pair of the wires 19 and 19' can be connected to the dial 40 through the connection pipe. By the connection structure between a pair of the wires 19 and 19' and the dial 40, if the handle portion 22 of the main body 20 is gripped to turn the dial 40 clockwise and pull out the right wire 19, the insertion part 10 can be bent to the right, or if the handle portion 22 is gripped to turn the dial 40 counterclockwise and pull out the left wire 19', the insertion part 10 can be bent to the left. The outer periphery of the dial 40 may be provided with unevenness for preventing operation errors such as slippage.

Figure 3A:
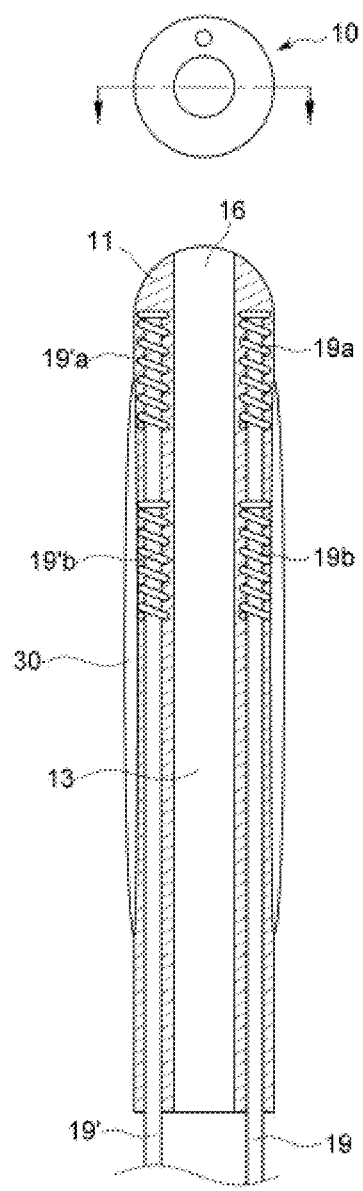
Figure 3B:
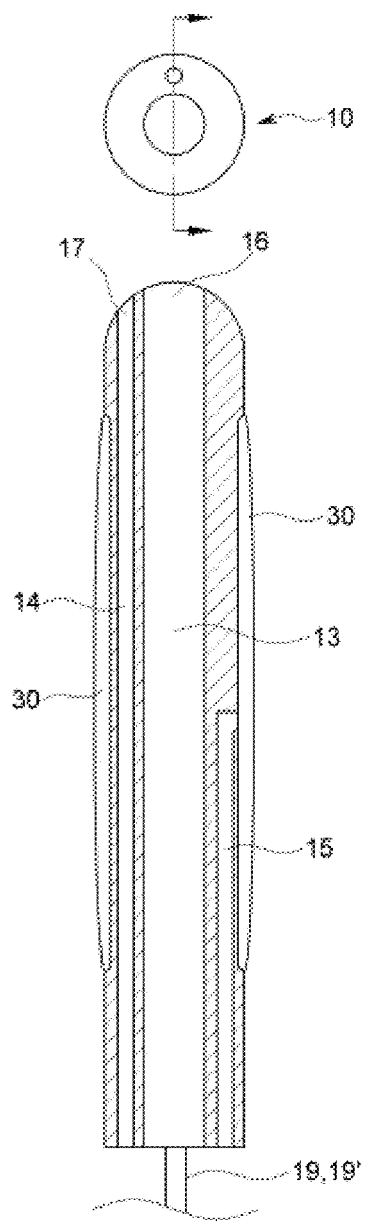

At least one end among a pair of the wires 19 and 19' may include a fixed tip portions 19 a, 19 b, 19'a & 19'b having a spring shape or a concave-convex shape so as to be more firmly fixed to a region of the first end 11 of the insertion part 10. The fixed tip portions 19 a, 19 b, 19'a & 19'b may include either one fixed tip portion having a spring shape or a concavo-convex shape, or a plurality of fixed tip portions spaced apart from each other with regular intervals at one end of the wire, as shown in FIGS. 3a, 3a1, and 3a2. When heat is externally applied for manufacturing the medical apparatus 1, the material (e.g., plastic) of the insertion part melts into between the springs or the irregularities of the fixed tip portions 19 a, 19 b, 19'a & 19'b or between a plurality of the fixed tip portions and is hardened finally to more securely fix the wire to the insertion portion 10.

The insertion part 10 may include an expansion part 30 configured to be expandable near the first end 11 which is inserted into the human body. More specifically, the expansion part 30 is formed on an outer surface of the insertion part 10 at a predetermined distance apart from the first end 11 of the insertion part 10.

The expansion part 30 may be configured to have substantially the same plane as the outer surface of the insertion part 10. In this case, when the insertion part 10 is inserted, it is possible to prevent damage to a tissue in the human body or to prevent the insertion part 10 from being caught in the body.

Figure 4:
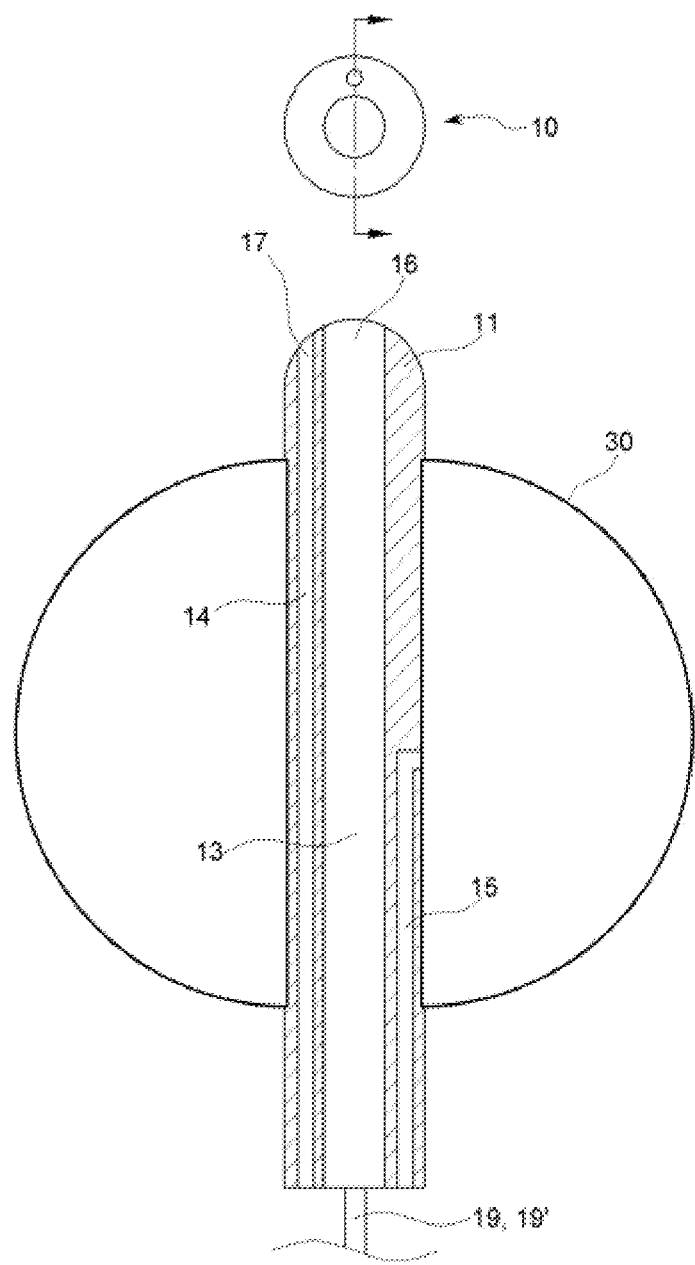
FIG. 4 is a view showing an expanded state of an expansion part according to an embodiment of the present invention.

FIG. 4 is a view showing an expanded state of an expansion part according to one embodiment of the present invention. The expansion of the expansion part 30 can be accomplished by supplying or applying a fluid to the expansion part 30. As shown in FIG. 4, when the expansion part 30 is expanded, the expansion part 30 protrudes from the outer surface of the insertion part 10. Accordingly, under the state that the insertion part 10 is inserted into the body during a surgery procedure, such expansion of the expansion part 30 can physically and efficiently alleviate the adhesion to the epidural space or the stenosis to the spinal canal.

An expansion part-passage 15 communicating with the expansion part 30 may be formed inside the insertion part 10 and an expansion part-connecting unit 23 communicating with the expansion part-passage 15 may be formed in the main body 20. An input unit (e.g., a fluid-supply source for supplying a fluid, a syringe, an operating switch for expanding the expansion part, a handle, etc.) capable of expanding the expansion part 30 can be connected to the expansion part-connecting unit 23.

Figure 5A:
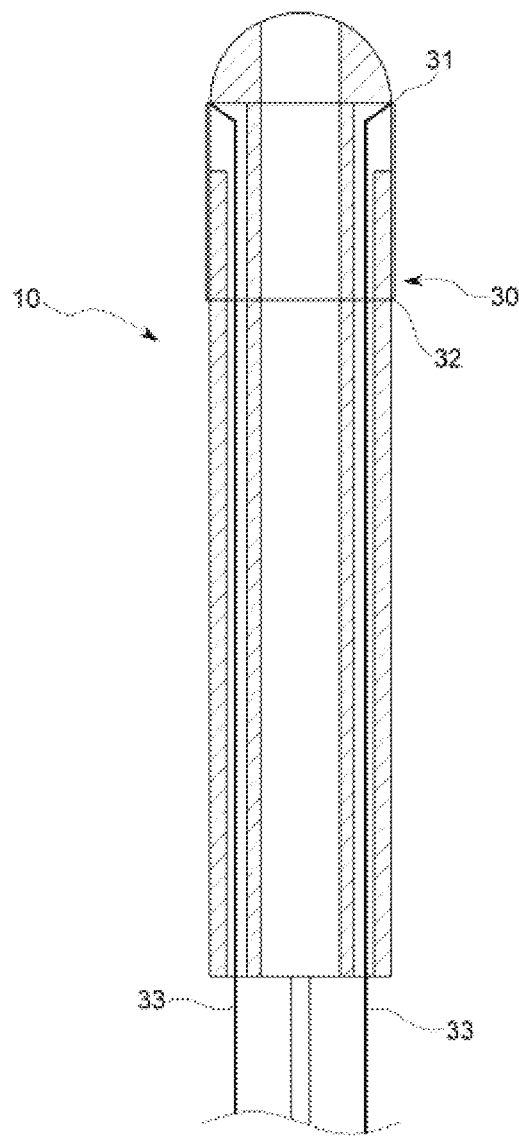
FIGS. 5a, 5b and 5c are diagrams illustrating an operation of an expansion part configured to be an expansion structure made of a mesh structure according to an embodiment of the present invention.
Figure 5B:
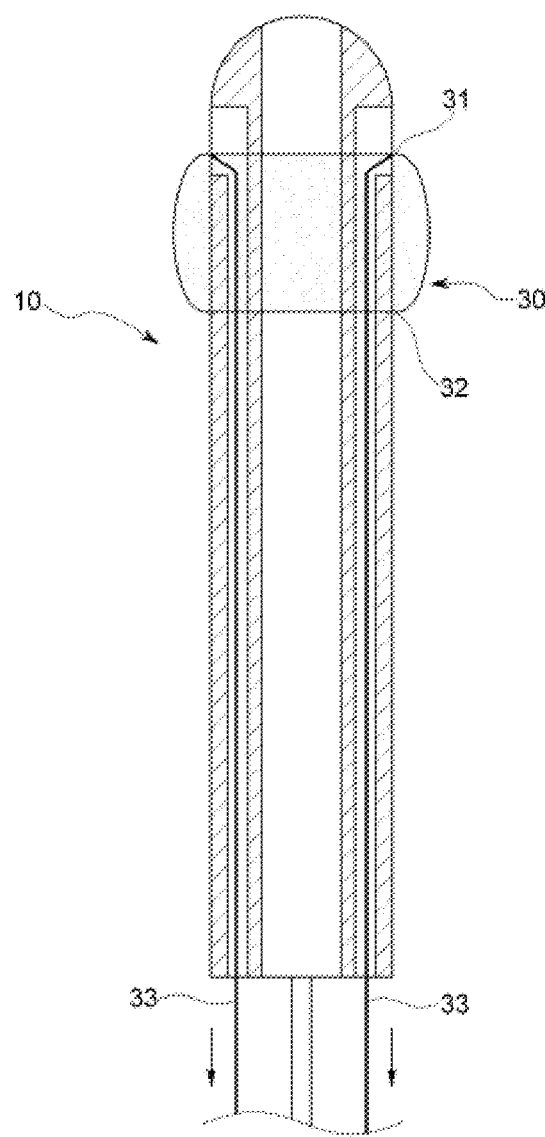
Figure 5C:
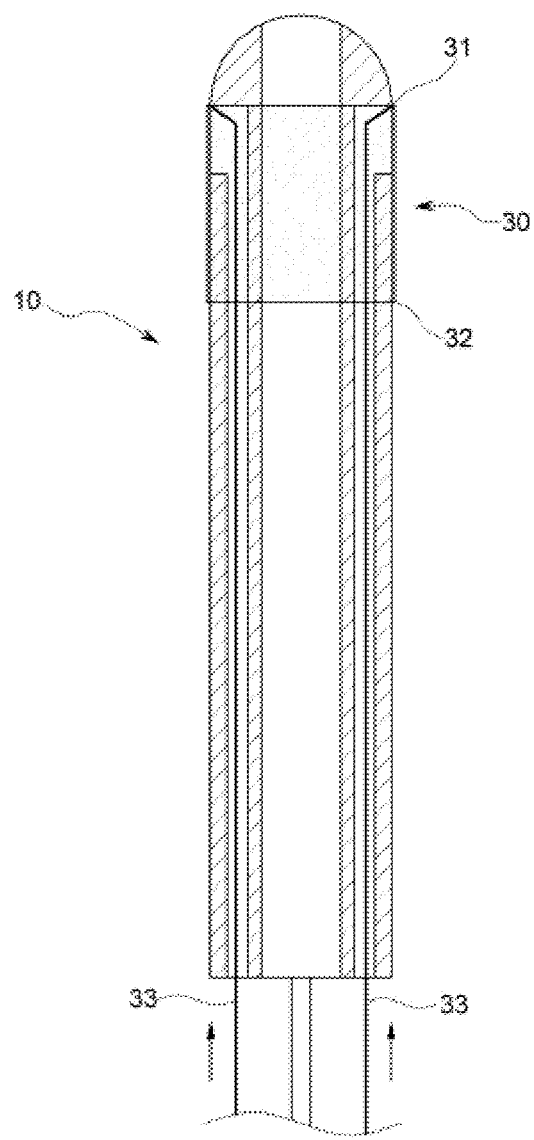
Figure 5D:
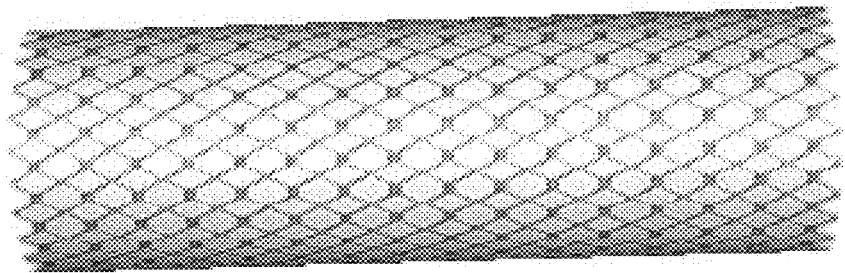
FIG. 5d is a view showing an expansion structure made of a mesh structure according to an embodiment of the present invention.

FIGS. 5a to 5c are diagrams illustrating an operation of an expansion part 30 configured to be an expansion structure made of a mesh structure according to an embodiment of the present invention, and FIG. 5d is a view showing an expansion structure having a mesh structure according to an embodiment of the present invention. As shown in FIGS. 5a to 5d, according to an embodiment of the present invention, the expansion part 30 is the expansion structure made of the mesh structure.

The expansion structure is preferably made of a radiation-impermeable material. For example, the expansion structure may be designed to include a radiation-impermeable material such as a thin wire. In virtue of the above, the expansion structure is very effective in a surgical procedure, since it can be confirmed through a radioscopic apparatus during the procedure. Further, it is preferred that the expansion structure includes a biomedical metallic material having a strong resilience such as NiTi. The insertion part 10 may also be made of such materials.

The expansion of the expansion structure is performed by an expansion structure wire 33. The expansion structure wire 33 is provided inside the insertion part 10, one end of which is connected to an expansion structure. The expansion structure wire 33 may be extended through an expansion part-passage 15.

The expansion structure may include a first end region 31 directed toward the first end 11 of the insertion part 10 and a second end region 32 directed toward the second end 12 of the insertion part 10. According to one embodiment of the present invention, the first end region 31 can be moved on the outer surface of the insertion part 10 without being fixed. On the other hand, the second end region 32 is fixed to the outer surface of the insertion part 10. In this case, the expansion structure wire 33 may be connected to the first end region 31 which is not fixed to the outer surface of the insertion part 10.

Referring to the expansion and contraction process of the expansion structure, as shown in FIG. 5a, the expansion structure in the initial state in which the expansion structure, i.e., the expansion part 30, of the mesh structure is not expanded, is formed on the outer surface of the insertion part 10 to be substantially flush with the outer surface of the insertion part 10. When the insertion part 10 is inserted into the human body and the expansion structure wire 33 is pulled in the direction of the second end 12 of the insertion part 10 during the surgical procedure, as shown in FIG. 5b, the first end region 31 to which the expansion structure wire 33 is connected can slide and move along the outer surface of the insertion part 10 in the direction approaching the second end region 32, whereby the expansion structure is expanded. Contrary to the above, when the expansion structure wire 33 is pushed toward the first end 11 of the insertion part 10, as shown in FIG. 5c, the first end region 31 to which the expansion structure wire 33 is connected can slide and move along the outer surface of the insertion part 10 in the direction away from the second end region 32, whereby the expansion structure is contracted.

The expansion structure wire 33 may be connected to a special handle (not shown) provided on the main body 20 by engaging with the expansion part-connecting unit 23. In this case, the operator can pull or push the expansion structure wire 33 by operating the handle. According to another embodiment, the special handle of the expansion structure wire 33 may be provided on a dial 40. According to this embodiment, the operator can control the direction of the insertion part 10 by operating the dial 40 with one hand, and can control the expansion or contraction of the expansion structure by operating the special handle of the expansion structure on the dial 40 without changing the position of the same hand. The special handle of the expansion structure may be the shape of a dial or a gear wheel that rotates around an axis. In this case, if the handle of the expansion structure is turned in one direction, the expansion structure wire 33 can be pulled, and if the handle of the expansion structure is turned in the opposite direction, the expansion structure wire 33 can be pushed. According to one aspect, the dial 40 and the handle of the expansion structure may have a structure that rotates independently of each other while sharing the same rotation axis.

When the expansion part 30 is used as an expansion structure made of a mesh structure, the adhesion to an epidural space or the stenosis to a spinal canal in the body can be alleviated physically. In addition, there is no risk of damage to the body due to a sharp object, and it is possible to positively perform the surgical procedure by the expansion part having a high strength.

According to another embodiment of the present invention, the expansion part 30 may be expanded with a fluid supply. The fluid may be supplied to the expansion part 30 from a fluid supply source provided inside or outside the medical apparatus 1 through an expansion part-passage 15. According to one embodiment, the fluid supply source may utilize a fluid supply device that can be attached to and detached from an expansion part-connecting unit 23. In this case, as much as the volume of the fluid supply device is reduced, the fluid is supplied from the fluid supply device to the expansion part 30 via the expansion part-connecting unit 23 and the expansion part-passage 15 to expand the expansion part 30. Accordingly, the expansion of the expansion part 30 can be attained as much as desired by controlling the amount of pressurization of the fluid supply device.

The fluid in the fluid supply source may contain a contrast medium. When the expansion part 30 is expanded by supplying the contrast medium to the expansion part 30, the degree of expansion of the expansion part 30 can be easily confirmed by a radioscopic apparatus.

Figure 6:
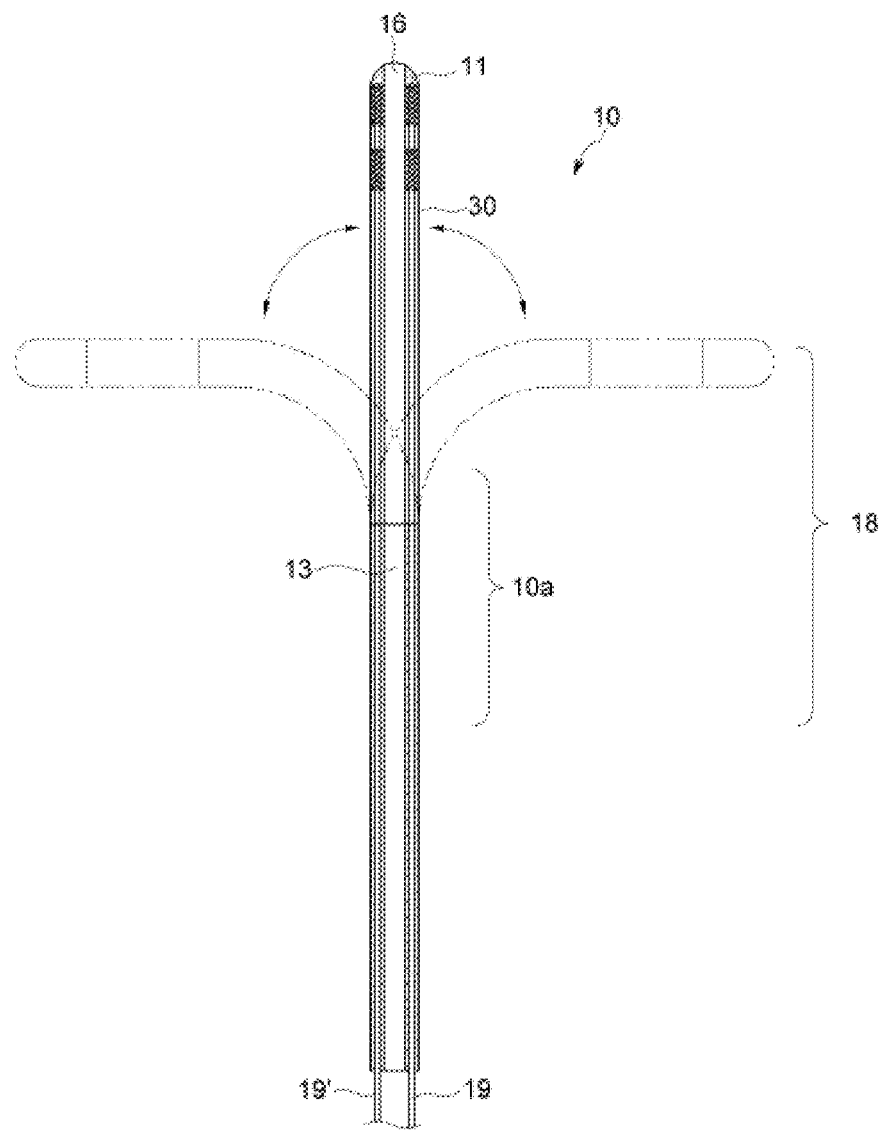
FIG. 6 is a view showing the operation of an end portion of the insertion part in a medical apparatus according to an embodiment of the present invention.

FIG. 6 is a view showing the operation of the end portion of the insertion part 10 in a medical apparatus 1 according to the embodiment of the present invention. As shown in FIG. 6, the insertion part 10 may have a movable end 18 formed therein. The insertion part 10 is configured to cause the bending in the region of the movable end 18 through the rotation operation of the dial 40 to which a pair of the wires 19 and 19' are connected. According to one embodiment, the insertion part 10 includes a soft portion 10a formed of a flexible material between the expansion part 30 and the second end 12 of the insertion part 10. Since such soft portion 10a is much flexible compared to other portions of the insertion part 10, the soft portion 10a is bent when the dial 40 is rotated. In this case, since the expansion part 30 and the soft portion 10a are independently driven, if necessary, the expansion operation of the expansion part 30 and the bending operation of the movable end 18 through the soft portion 10a can be performed at the same time.

FIGS. 7a to 8b are diagrams showing the operating relationship between a dial 40 and a rotation control part 41 of a medical apparatus 1 according to the embodiment of the present invention. As illustrated in FIGS. 7a to 7d, to the dial 40 may be connected a rotation control part 41 that can limit the rotation of the dial 40 so that the dial 40 is not rotated over a certain angle.

The rotation control part 41 may include at least one of a first rotation control unit 41a that allows the dial 40 to rotate at a first angle or less and a second rotation control unit 41b that allows the dial 40 to rotate at a second angle or less. The first angle and the second angle are different from each other.

Figure 7A:
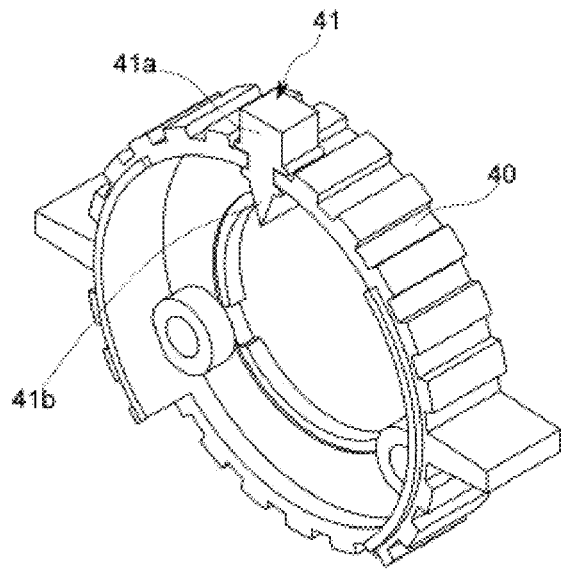
FIGS. 7a, 7b, 7c and 7d are views showing the positioning of a rotation control part for a dial in a medical apparatus according to an embodiment of the present invention.
Figure 7B:
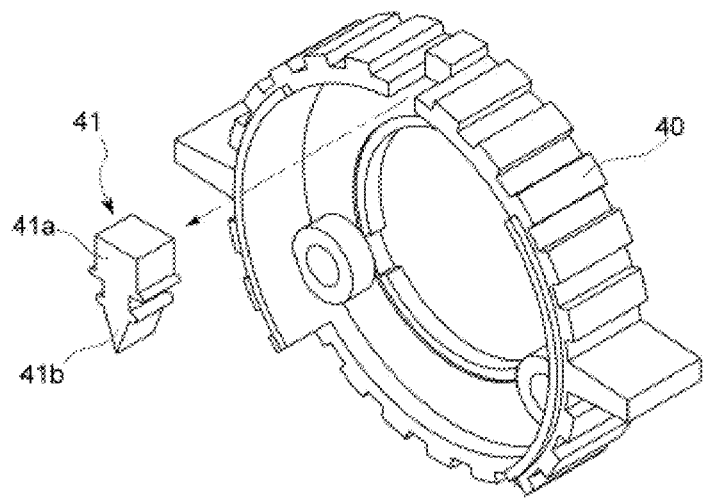
Figure 7C:
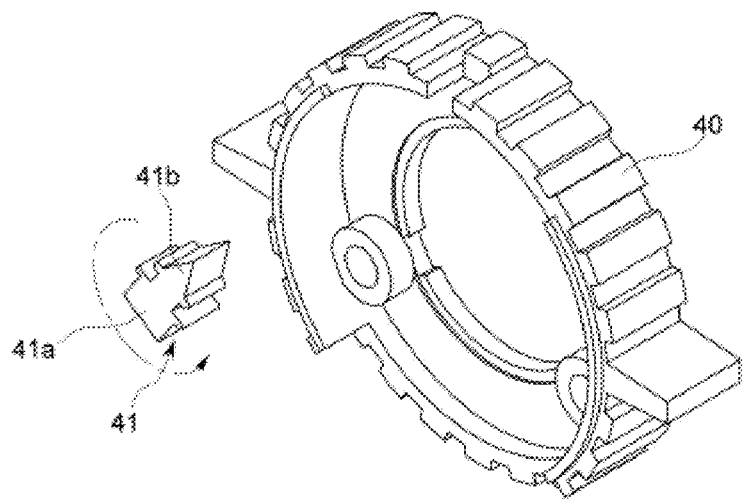
Figure 7D:
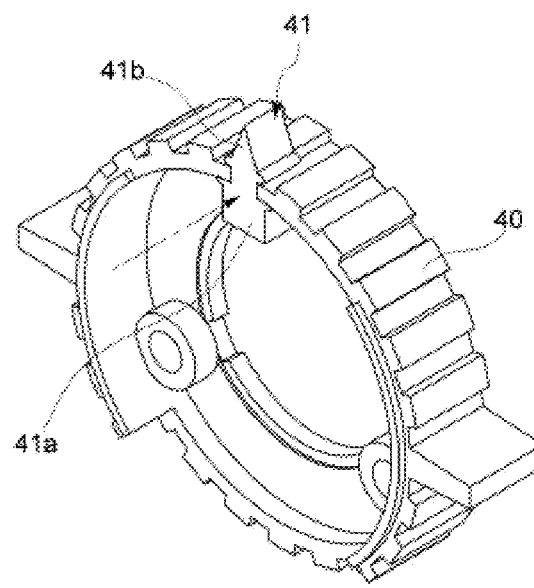

According to an embodiment of the present invention, as shown in FIG. 7a, the rotation control part 41 includes both the first rotation control unit 41a and the second rotation control unit 41b. The thickness in the dial rotation direction of the first rotation control unit 41a is configured to be thicker than the thickness in the dial rotation direction of the second rotation control unit 41b.

Figure 8A:
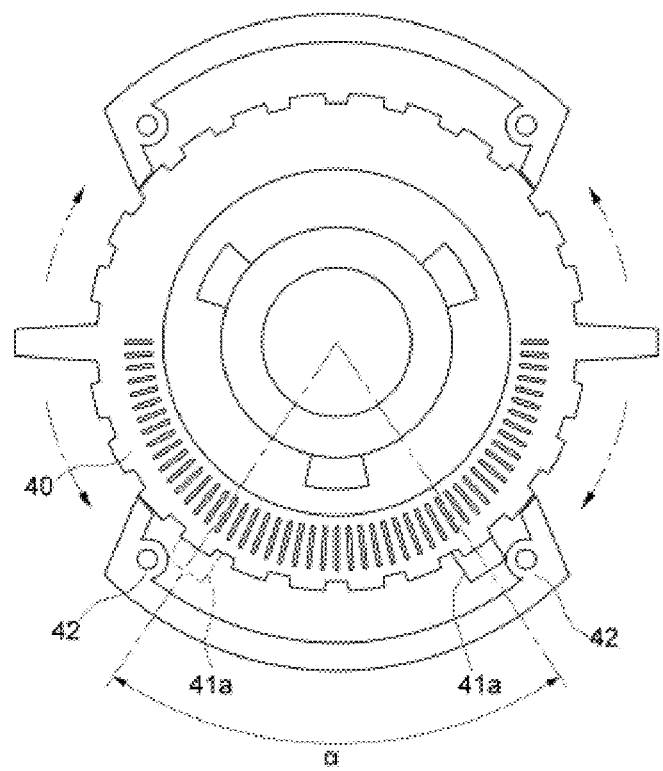
FIGS. 8a and 8b are views showing a rotatable range depending on the rotation restriction of a dial according to an embodiment of the present invention.

The rotation control part 41 can be positioned on the dial 40 such that the first rotation control unit 41a protrudes outwardly of the dial 40 and the second rotation control unit 41b protrudes inwardly of the dial 40. When the position of the rotation control part 41 is set so that one control unit protrudes outside the dial 40 as described above, the dial 40 can rotate within a range in which the first rotation control unit 41a is not caught by a stopper 42 as shown in FIG. 8a. The stopper 42 may be integrally formed with the main body 20 or be provided as a separate element. In addition, the stopper 42 is equipped on the rotation path of the dial 40 to contact the first rotation control unit 41a, thereby restricting the rotation of the dial 40. When the first rotation control unit 41a is in a position capable of contacting the stopper 42, the dial 40 is rotatable at a first angle (α).

Figure 8B:
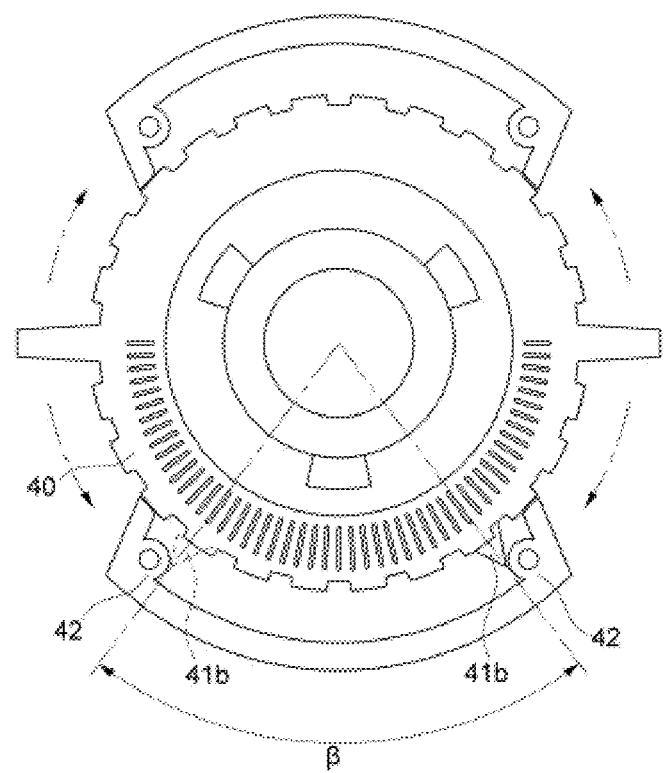

According to other embodiment, the rotation control part 41 can be positioned on the dial 40 such that the second rotation control unit 41b protrudes outwardly of the dial 40 and the first rotation control unit 41a protrudes inwardly of the dial 40. Therefore, as shown in FIG. 8b, the dial 40 can be rotated within a range in which the second rotation control unit 41b is not caught by the stopper 42. The stopper 42 restricts the rotation of the dial 40 by contacting the second rotation control unit 41b. When the second rotation control unit 41b is in a position capable of contacting the stopper 42, the dial 40 is rotatable at a second angle (β).

The first angle (α) and the second angle (β) are different in size from each other. Therefore, considering a limited range of the rotation desired for the dial 40 to the extent that bleeding in the human body does not occur by the operation of the movable end 18 of the insertion part 10, the position of the rotation control part 41 may be set such that the first rotation control unit 41a or the second rotation control unit 41b is placed alternatively at a position capable of contacting the stopper.

The rotation control part 41 may be formed as a separate member from the dial 40 to be detached from or attached to the dial 40. In this case, as shown in FIGS. 7a to 7d, when the position of the rotation control part 41 is set so that the first rotation control unit 41a is placed at the position protruding outside the dial 40, the rotation control part 41 can be set to be placed at the position where the second rotation control unit 41b protrudes outside the dial 40 by separating the rotation control part 41 from the dial 40. By the above, it is possible to replace only the rotation control part 41 depending on the rotation restriction range of the dial 40 by modulating the rotation control part 41, and to repair and exchange the rotation control part 41 readily.

The main body 20 may be provided with a fixing switch 26 for fixing the rotation of the dial 40. The fixing switch 26 is provided to be capable of being engaged or disengaged with the dial 40 depending on the up and down movement thereof. The bending state of the movable end 18 can be maintained by fixing the rotation of the dial 40 with the fixing switch 26 at an appropriate position, as necessary, when the movable end 18 of the insertion part 10 is operated.

Figure 9:
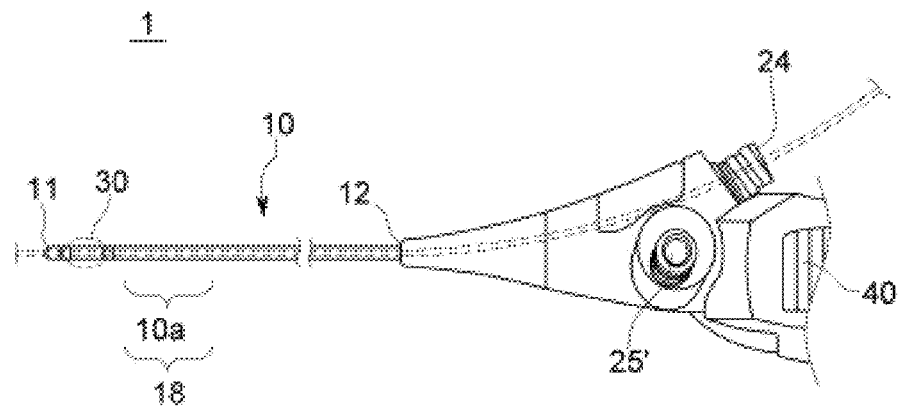
FIG. 9 is a view showing the use state of a medical apparatus according to the embodiment of the present invention.

FIG. 9 is a view showing a use state of a medical apparatus 1 according to an embodiment of the present invention. As shown in FIG. 9, a first injection port 24 capable of injecting a drug or inserting a medical instrument in communication with a first through hole 13 is provided between the second end 12 of the insertion part 10 and the dial 40. Therefore, a catheter for injecting the drug or an endoscope can be inserted into the first injection port 24 and protruded outside the first hole 16 via the first through hole 13. The first injection port 24 may be positioned proximate to the front portion of the main body 20, that is, the portion to which the insertion part 10 and the main body 20 are connected. The length of the insertion part 10 inserted into the human body can be reduced by positioning the first injection port 24 at the front of the body 20, and since the first injection port 24 is positioned in front of the handle portion 22 of the main body 20, the operator can facilitate the injection of a drug or a catheter, or an imaging operation by an endoscopic insertion through the first injection port 24.

In the case of using the medical apparatus 1, after the operator operates the expansion part 30 or the movable end 18 in the body and performs the physical dissociation, the operator can pull out the insertion part 10 by a predetermined distance (e.g., by the distance between the expansion part 30 or the movable end 18 and the first end 11 of the insertion part 10), and then effectively inject the drug into the physically dissociated region by injecting the drug directly or using the catheter.

Figure 10:
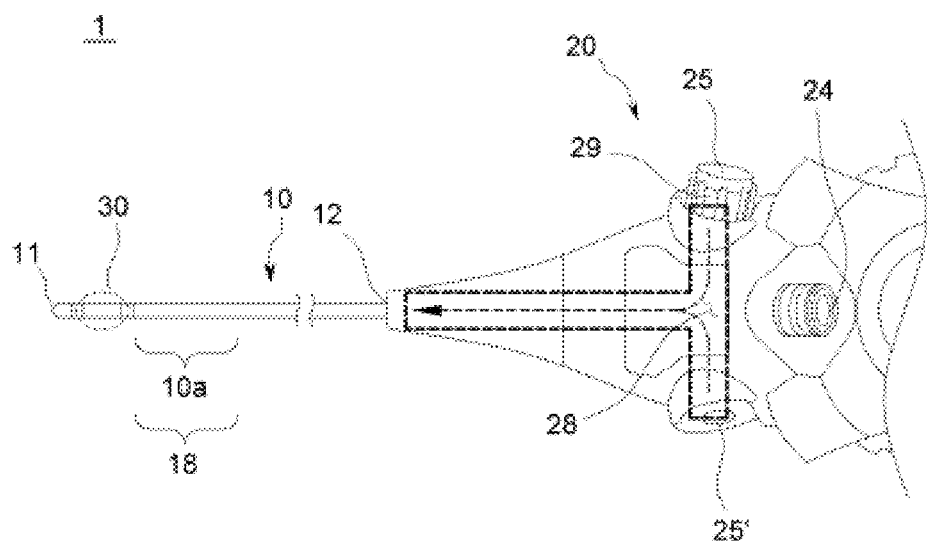
FIG. 10 is a view showing an internal passage of the main body according to an embodiment of the present invention.

FIG. 10 is a view showing an internal passage of a main body according to an embodiment of the present invention. As shown in FIG. 10, a pair of second injection ports 25, 25' may be provided on both sides of the first injection port 24, that is, on both outer sides of the main body 20 to inject a drug different from the drug injected into the first injection port 24 or inject an irrigation fluid for irrigating a medical instrument or a bleeding within the human body tissue. For example, when an endoscope is inserted into the first injection port 24 and protruded from the first hole 16 during a surgical procedure, the endoscope can be cleaned by injecting the irrigation fluid through a pair of the second injection ports 25, 25', and when the bleeding occurs in the human body due to the operation of a movable end 18, the bleeding within the human body tissue can be easily irrigated with the irrigation fluid. The irrigation fluid is supplied to a second hole 17 located adjacent to a first hole 16 via a pair of the second injection ports 25 and 25', the inner passage of the main body 20, and a second through hole 14, sequentially. The first hole 16 and the second hole 17 may be formed on the same side wall of the first end 11 of the insertion part 10. Since the first hole 16 and the second hole 17 are closely located adjacent to each other, the cleaning can be easily performed even with the supply of a small amount of the irrigation fluid.

The inner passage of the main body 20 communicating with a pair of the second injection ports 25, 25' can be formed by a T-shaped passage 28. In this case, a pair of the second injection ports 25 and 25' may be communicated with the short passage portion of the T-shaped passage 28 and the long passage portion of the T-shaped passage 28 may be communicated with the second through hole 14. Therefore, the operator can inject the irrigation fluid into the injection port of any one of a pair of the second injection ports 25, 25' regardless of the left-handed/right-handed person, and the irrigation fluid can flow into the second through hole 14. In case only one of the second injection ports 25, 25' should be used, the other injection port can be blocked by using the cap 29.

The expansion part-connecting unit 23 may be positioned between the first injection port 24 and the handle portion 22. During the procedure, it is preferred that the operator's moving line to the expansion part-connecting unit 23 and the first injection port 24 does not overlap each other. According to this, the expansion part-connecting unit 23 may have a structure that can rotate left and right or a pivot structure. For example, the expansion part-connecting unit 23 may not be connected to the main body 20 directly, but be connected to a fixing unit 27 between the main body 20. A bearing may be provided between the expansion part-connecting unit 23 and the fixing unit 27, or between these two units and the main body 20. Thus, a longitudinal axis of the expansion part-connecting unit 23 may be inclined on the basis of the body 20 together with the fixing unit 27.

When a fluid supply device is connected to the expansion part-connecting unit 23 in the state where the catheter for drug injection or the endoscope passes through the first injection port 24, the entry paths of the catheter (or the endoscope) and the fluid supply device can be prevented from crossing each other by rotating or pivoting the expansion part-connecting unit 23, thereby enabling the use of these instruments at the same time.

Further, although the expansion part-connecting unit 23 may be designed in its fixed state so that the entry paths of the catheter and the fluid supply device do not cross each other, it is also possible to prevent the entry path of the fluid supply device and the expansion part-connecting unit 23 from crossing each other by designing the expansion part-connecting unit 23 to make it rotatable or pivotable, regardless of whether the handle portion 22 is gripped with a left hand or a right hand.

As described above, the medical apparatus according to the embodiments of the present invention is mainly intended to dissociate the adherence to an epidural space and alleviate the stenosis to a spinal canal by inserting the insertion part 10 into the epidural space through coccygeal vertebra, but is not essentially limited thereto.

Although the present invention has been described based on the foregoing embodiments and the accompanying drawings for the purpose of illustration only, it is to be understood that the protection scope of the present invention is defined by the appended claims. It will be appreciated by a person who has an ordinary knowledge in the relevant art that the invention may be embodied in many different forms such as a simple substitution, modification and change without being beyond the scope of the appended claims.

What is claimed is:

1. A medical apparatus comprising:
   an insertion part including a first end configured to be inserted into a human body and a second end opposite to the first end, and having a first through hole extended from the first end to the second end and formed inside the insertion part,
   an expansion part configured to be expandable and formed on an outer surface of the insertion part at a predetermined distance apart from the first end of the insertion part,
   a pair of wires extending in the insertion part and fixed to a region of the first end of the insertion part, the pair of wires being capable of causing bending of the insertion part by pulling out at least one of the wires,
   a main body connected to the insertion part at the second end thereof,
   a dial installed to the main body rotatably and connected to the pair of wires, and
   a rotation control part coupled to the dial, and configured to limit rotation of the dial so that the dial is not rotated over a predetermined angle;
   wherein at least one of the pair of wires has a plurality of spring shapes or concave-convex shapes extending along a longitudinal direction at a portion fixed to the region of the first end of the insertion part,
   wherein the rotation control part includes a first rotation control unit and a second rotation control unit, wherein the first rotation control unit allows the dial to rotate at a first angle or less and the second rotation control unit allows the dial to rotate at a second angle or less different from the first angle, and wherein the first rotation control unit and the second rotation control unit are formed integrally.

2. The medical apparatus according to claim 1, wherein the first rotation control unit or the second rotation control unit contacts a stopper formed on the main body to limit the rotation of the dial.

3. The medical apparatus according to claim 2, wherein a position of the rotation control part can be set such that one of the first rotation control unit and the second rotation control unit is placed at a position that is in contact with the stopper.

4. The medical apparatus according to claim 1, wherein the expansion part is an expansion structure made of a mesh structure.

5. The medical apparatus according to claim 4, wherein the expansion structure is composed of a radiation-impermeable material.

6. The medical apparatus according to claim 4, wherein an expansion structure wire for expanding or contracting the expansion structure is provided inside the insertion part, and one end portion of the expansion structure wire is connected to the expansion structure.

7. The medical apparatus according to claim 6, wherein the expansion structure includes a first end region directing toward the first end of the insertion part and a second end region directing toward the second end of the insertion part, wherein the first end region is not fixed to the insertion part, the second end region is fixed to the insertion part, and the expansion structure wire is connected to the not fixed first end region.

8. The medical apparatus according to claim 1, comprising a first injection port formed between the second end of the insertion part and the dial and communicating with the first through hole to inject a drug or insert a medical instrument, and a pair of second injection ports formed on both sides of the first injection port, respectively, to inject a drug different from the drug injected into the first injection port or an irrigation fluid.

9. The medical apparatus according to claim 8, wherein the pair of second injection ports communicate with a T-shaped passage formed inside the main body, and the T-shaped passage communicates with a second through hole formed inside the insertion part.

10. The medical apparatus according to claim 1, wherein the insertion part includes a flexible portion made of a flexible material between the expansion part and the second end of the insertion part.

11. The medical apparatus according to claim 1, wherein the at least one of the pair of wires has the plurality of spring shapes or concave-convex shapes spaced apart from each other at a regular interval at the portion fixed to the region of the first end of the insertion part.

12. The medical apparatus according to claim 1, wherein the at least one of the pair of wires has the plurality of spring shapes or concave-convex shapes spaced apart from each other at a regular interval in the longitudinal direction at the portion fixed to the region of the first end of the insertion part.

* * * * *